(12) United States Patent
Schouenborg

(10) Patent No.: US 11,771,356 B2
(45) Date of Patent: Oct. 3, 2023

(54) MICROELECTRODE ARRAY COMPRISING CONNECTING MICROFIBERS

(71) Applicant: NEURONANO AB, Karlshamn (SE)

(72) Inventor: Jens Schouenborg, Lund (SE)

(73) Assignee: NEURONANO AB (SE)

( * ) Notice: Subject to any disclaimer, the term of this patent is extended or adjusted under 35 U.S.C. 154(b) by 1083 days.

(21) Appl. No.: 16/465,595

(22) PCT Filed: Nov. 29, 2017

(86) PCT No.: PCT/SE2017/000048
§ 371 (c)(1),
(2) Date: May 31, 2019

(87) PCT Pub. No.: WO2018/106165
PCT Pub. Date: Jun. 14, 2018

(65) Prior Publication Data
US 2019/0380603 A1    Dec. 19, 2019

(30) Foreign Application Priority Data

Dec. 5, 2016    (SE) .................................. 16000334-5

(51) Int. Cl.
*A61B 5/24*    (2021.01)
*A61B 5/00*    (2006.01)
(Continued)

(52) U.S. Cl.
CPC .............. *A61B 5/24* (2021.01); *A61B 5/6877* (2013.01); *D04H 1/435* (2013.01);
(Continued)

(58) Field of Classification Search
CPC ................ A61N 1/0551; A61N 1/0558; A61N 1/05–0597; D04H 1/4334; D04H 1/435;
(Continued)

(56) References Cited

U.S. PATENT DOCUMENTS

| 8,182,496 B2 | 5/2012 | Rudd et al. ................... 606/151 |
| 2005/0273138 A1 | 12/2005 | To et al. ....................... 606/219 |

(Continued)

FOREIGN PATENT DOCUMENTS

| CN | 101888873 B | 3/2015 |
| CN | 104760922 B | 8/2016 |

(Continued)

OTHER PUBLICATIONS

Welz, Mary M., and Clyde M. Ofner. "Examination of Self-Crosslinked Gelatin as a Hydrogel for Controlled Release." Journal of Pharmaceutical Sciences, vol. 81, No. 1, Jan. 1992, pp. 85-90., https://doi.org/10.1002/jps.2600810117. (Year: 1992).*

(Continued)

*Primary Examiner* — Larissa Rowe Emrich
(74) *Attorney, Agent, or Firm* — OSTROLENK FABER LLP

(57) ABSTRACT

A microelectrode array comprises three or more flexible oblong, electrically co-operating microelectrodes in wire and/or ribbon form disposed substantially in parallel. The microelectrodes are electrically insulated except for at a distal section thereof. The array further comprises electrically non-conducting microfibres connecting central portions of the microelectrodes in oblique directions in respect of the array axis. In a preferred array variety the microelectrodes are joined by a glue that is dissolvable or degradable in aqueous body fluid. Also disclosed is a combination of two or more arrays of the invention.

32 Claims, 8 Drawing Sheets

Figure 1A:
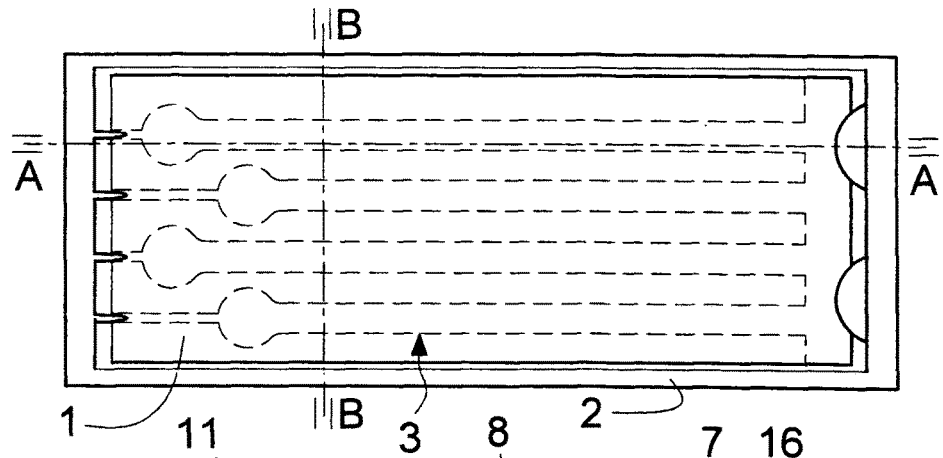

(51) Int. Cl.
*D04H 1/728* (2012.01)
*D04H 1/4334* (2012.01)
*D04H 1/435* (2012.01)
*D04H 1/587* (2012.01)

(52) U.S. Cl.
CPC .......... *D04H 1/4334* (2013.01); *D04H 1/587* (2013.01); *D04H 1/728* (2013.01); *A61B 2562/028* (2013.01); *A61B 2562/043* (2013.01); *D10B 2211/20* (2013.01); *D10B 2401/12* (2013.01); *D10B 2509/00* (2013.01)

(58) Field of Classification Search
CPC .......... D04H 1/587; D04H 1/728; A61B 5/24; A61B 5/42; A61B 5/685; A61B 5/6877; A61B 2562/028; A61B 2562/043; A61B 2562/0219; A61B 5/6868; A61B 5/4064; A61B 5/27; A61B 5/40–4094
See application file for complete search history.

(56) References Cited

U.S. PATENT DOCUMENTS

| | | | |
|---|---|---|---|
| 2010/0100152 A1 | 4/2010 | Martens et al. | 607/45 |
| 2011/0009728 A1* | 1/2011 | Schouenborg | A61N 1/0551 607/116 |
| 2011/0087315 A1 | 4/2011 | Richardson-Burns et al. | 607/116 |
| 2012/0123318 A1* | 5/2012 | Ek | A61N 1/325 604/20 |
| 2012/0271331 A1* | 10/2012 | To | A61B 17/0401 606/151 |
| 2012/0310140 A1 | 12/2012 | Kramer et al. | 604/20 |
| 2013/0090542 A1 | 4/2013 | Kipke et al. | 600/377 |
| 2014/0309548 A1 | 10/2014 | Merz et al. | 600/554 |
| 2015/0088222 A1 | 3/2015 | Bettinger | 607/40 |
| 2016/0270279 P1* | 9/2016 | O'Connell | A01H 5/02 Plt./263.1 |
| 2016/0270729 A1* | 9/2016 | Dvir | A61B 5/4848 |

FOREIGN PATENT DOCUMENTS

| | | |
|---|---|---|
| CN | 104411360 B | 6/2017 |
| JP | 2012-529338 A | 11/2012 |
| JP | 7095897 B | 6/2022 |
| WO | WO 2007/040442 A1 | 4/2007 |
| WO | WO 2009/075625 A1 | 6/2009 |
| WO | WO 2010/144016 A1 | 12/2010 |
| WO | WO 2013/191612 A1 | 12/2013 |
| WO | WO 2016/032384 A1 | 3/2016 |

OTHER PUBLICATIONS

Phillips, G.O. Williams, P.A . . . (2009). Handbook of Hydrocolloids (2nd Edition)—6.3.1 Bloom strength—standard method for characterizing gel strength. Woodhead Publishing. Retrieved from https://app.knovel.com/hotlink/pdf/id:kt006R7MD5/handbook-hydrocolloids/viscosity (Year: 2009).*
International Search Report dated Mar. 15, 2018 in corresponding PCT International Application No. PCT/SE2017/000048.
Written Opinion dated Mar. 15, 2018 in corresponding PCT International Application No. PCT/SE2017/000048.
G. Lind et al., "Gelatine-embedded electrodes—a novel biocompatible vehicle allowing implantation of highly flexible microelectrodes," Journal of Neural Engineering, vol. 7, 10 pages (2010).
B.C. DiPaolo et al., "Nanofiber scaffolding for improved neural electrode biocompatibility," Proceedings of the IEEE 29th Annual Northeast Bioengineering Conference, US 2003, p. 21-22.
Darrell H. Reneker et al., "Nanometre diameter fibres of polymer, produced by electrospinning", Nanotechnology (1996), vol. 7, pp. 216-223.
Michelle K. Leach et al., "Electrospinning Fundamentals: Optimizing Solution and Apparatus Parameters", Journal of Visualized Experiments (2011), vol. 47, pp. 1-4.
Raikishore Nayak et al., "Recent advances in nanofibre fabrication techniques", Textile Research Journal (2011), vol. 82, No. 2, pp. 129-147.
Natalia Davidenko et al., "Optimisation of UV irradiation as a binding site conserving method for crosslinking collagen-based scaffolds", J Mater Sci: Mater Med (2016), vol. 27, No. 14, pp. 1-17.
Evan M. Masutani et al. "Increasing Thermal Stability of Gelatin by UV-Induced Cross-Linking with Glucose", International Journal of Biomaterials (2014), pp. 1-10.
Jamil A. Matthews et al. "Electrospinning of Collagen Nanofibers", Biomacromolecules (2002), vol. 3 (2002), pp. 232-238.
C. Viney et al., "Inspiration versus duplication with biomolecular fibrous materials: learning nature's lessons without copying nature's limitations", Current Opinion in Solid State and Materials Science (2004), vol. 8, pp. 165-171.
Perumcherry Raman Sreerekha MSc et al., "Fabrication of Electrospun Poly (Lactide-co-Glycolide)-Fibrin Multiscale Scaffold for Myocardial Regeneration In Vitro", Tissue Engineering: Part A (2012), vol. 19, Nos. 7 and 8, pp. 849-859.
Sreerekha Raman Perumcherry M.Sc. et al., "A Novel Method for the Fabrication of Fibrin-Based Electrospun Nanofibrous Scaffold for Tissue-Engineering Applications", Tissue Engineering: Part C (2011), vol. 17, No. 11, pp. 1121-1130.
EPO Communication pursuant to Article 94(3) dated Oct. 1, 2021 issued in corresponding European Patent Application No. 17878865.9.
Supplementary European Search Report dated May 4, 2020 issued in corresponding European Patent Application No. 17878865.9.
European Search Opinion dated May 13, 2020 issued in corresponding European Patent Application No. 17878865.9.
Office Action dated Jul. 29, 2021 in corresponding Japanese Patent Application No. 2019-529999 and its English translation.
Office Action dated Nov. 29, 2022 in corresponding Chinese Patent Application No. 201780075207.7 and its English translation.

* cited by examiner

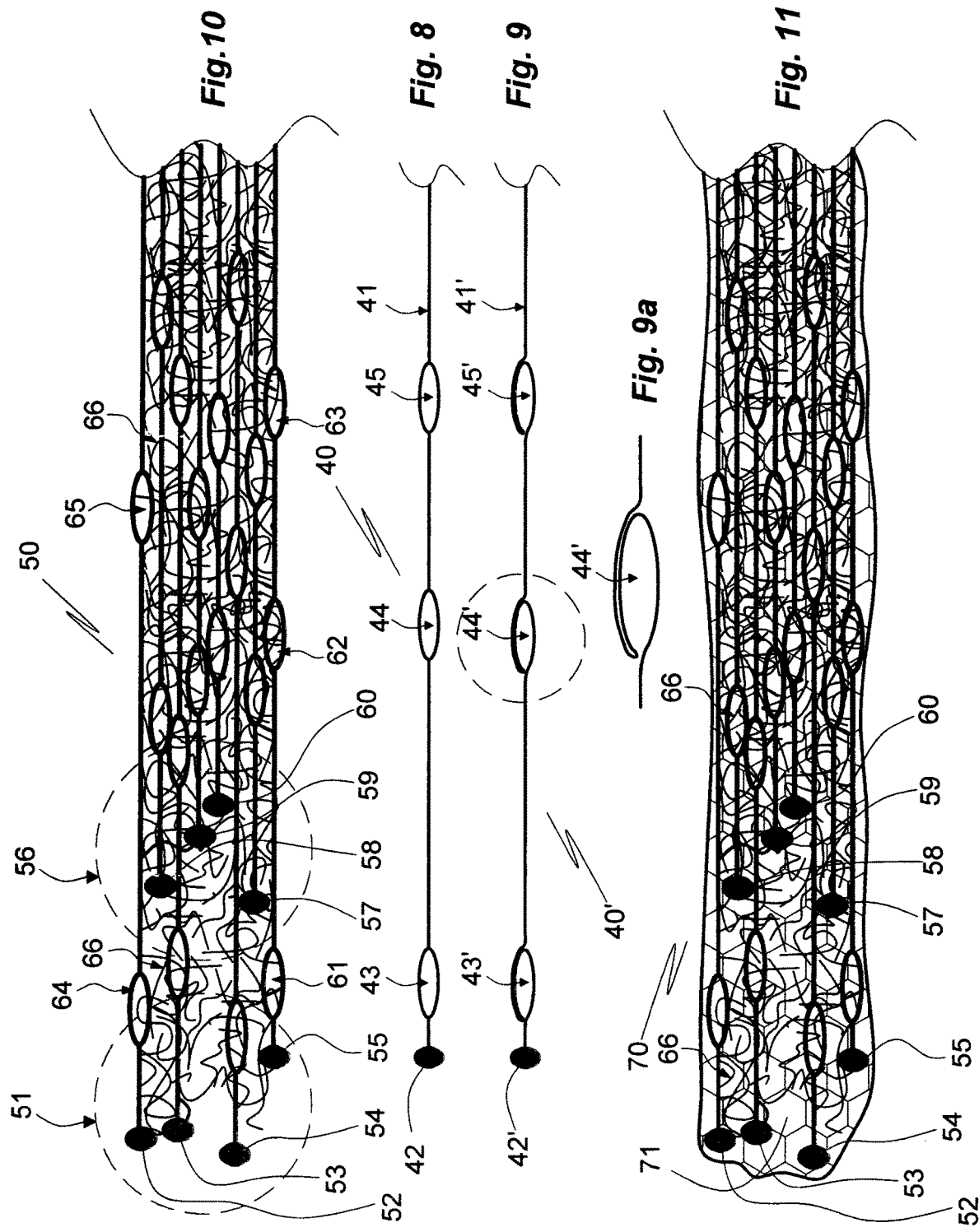

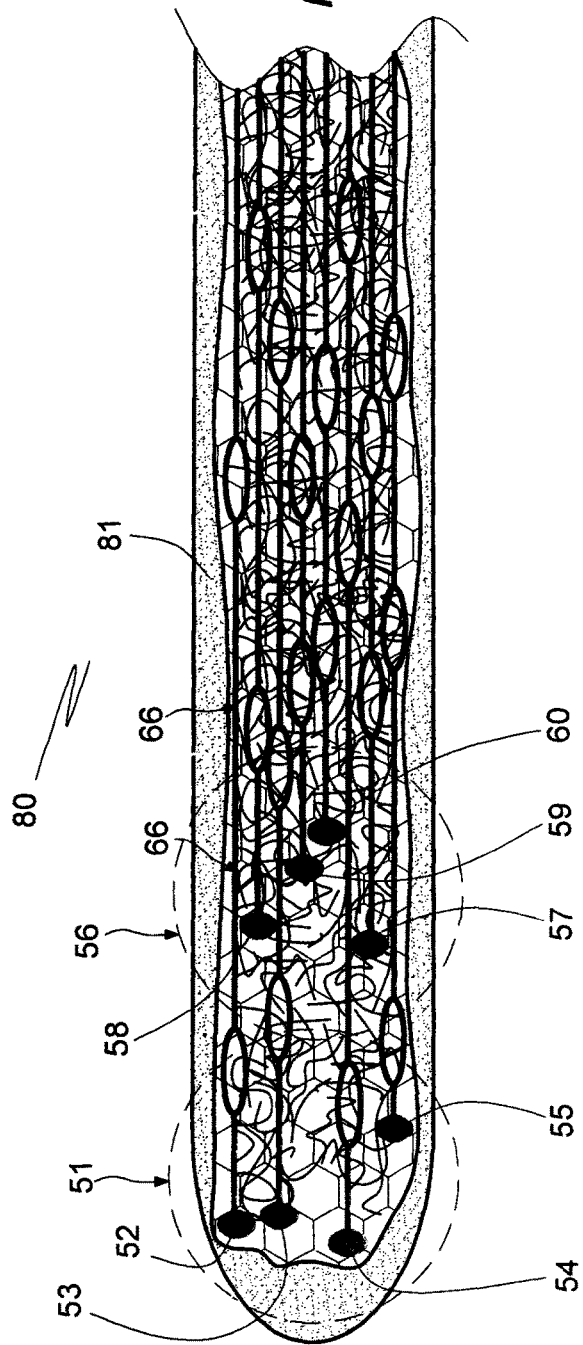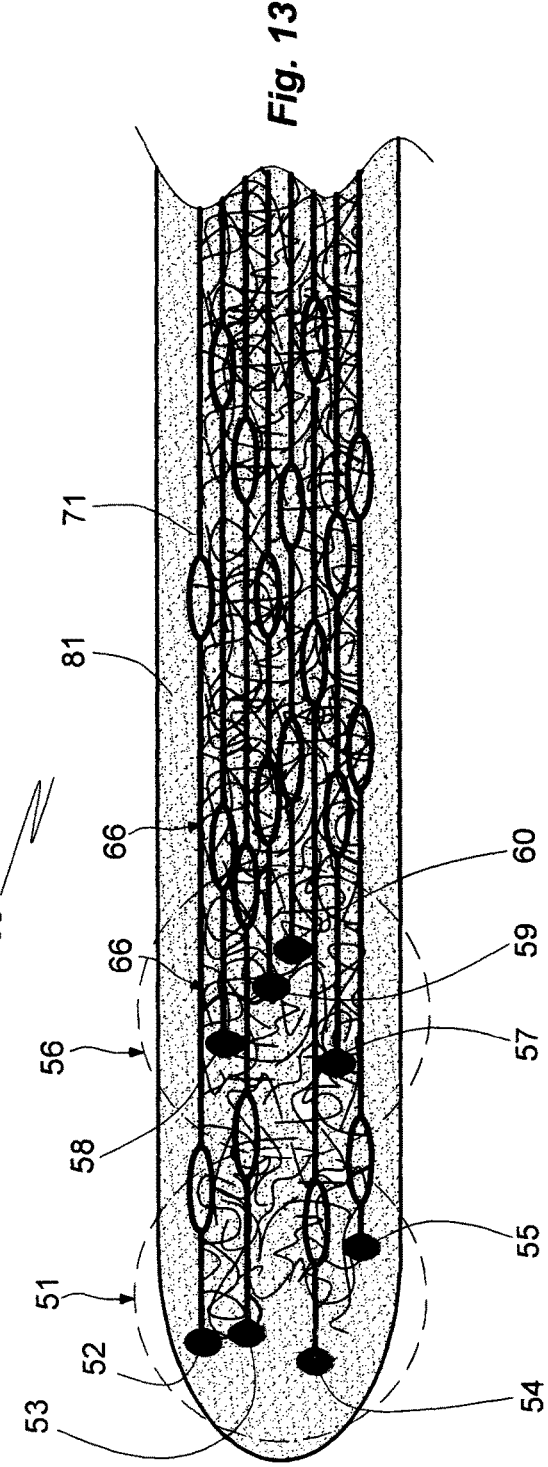

MICROELECTRODE ARRAY COMPRISING CONNECTING MICROFIBERS

CROSS-REFERENCE TO RELATED APPLICATIONS

The present application is a 35 U.S.C. §§ 371 national phase conversion of PCT/SE2017/000048, filed Nov. 29, 2017, which claims priority to Swedish Patent Application No. 16000334-5, filed Dec. 5, 2016, the contents of which are incorporated herein by reference. The PCT International Application was published in the English language.

FIELD OF THE INVENTION

The present invention relates to a microelectrode array, which integrates with soft tissue into which it has been implanted and which is capable of providing information about neighbouring neurons over long periods of time, and to a combination of such arrays. The present invention also relates to a microelectrode proto array, which is implantable into soft tissue and there is transformed to a microelectrode array of the invention. The present invention furthermore relates to a method for manufacture of the array, the combination of arrays and the proto array, to a method for their implantation, and to uses thereof.

BACKGROUND OF THE INVENTION

Implantable microelectrodes can be used for recording of electric signals emanating from excitable tissue such as nervous and endocrine tissue. A problem with implantable microelectrodes is their tendency to move within the tissue. Therefore, it is desirable to provide microelectrodes which, once implanted, are stable capable of remaining in their original position, that is, do not migrate. Positional stability of microelectrodes implanted into soft tissue is a prerequisite for long term studies of neural functions. Such long-term stability is necessary for studying or interacting with a learning process or a degenerative process.

It is also important for electrodes pertaining to such array to establish long term juxta membraneous communication to allow high fidelity recording as well as stimulation of specific neurons while avoiding exerting disturbing forces on nerve cell plasma membranes that might damage the membranes. It is known that glial reactions and survival of neighbouring nerve cells depend on the mechanical properties of the microelectrodes.

Furthermore, the positional stability of microelectrodes is important in identifying the neurons whose signals are being recorded. Recordings by use of single electrodes suffer from the uncertainty of identification the signal source. Action potentials originating from neurons of similar configuration such as, for instance, pyramidal cells in the cortex cerebri, tend to be rather similar in shape and amplitude for neurons located at about the same distance from the recording portion of an electrode that is, a non-insulated portion at or near its distal end. Thus, it cannot be ascertained by use of single microelectrodes whether a signal emanates from a particular neuron. While the use of pairs of microelectrodes improves the capability to discern between signals emanating from neighbouring nerve cells, it is only the use of a combination of least three, in particular of at least four microelectrodes that does allow precise determination.

In this application, a combination of at least three microelectrodes, in particular at least four microelectrodes, is called microelectrode array. The use of such an array and knowledge of signal attenuation with distance from a neuron in a triangulation method allows unequivocal determination of the spatial disposition of a neuron provided that the non-insulated portion(s) of a microelectrode comprised by the array are not disposed in one and the same plane. It is via these non-insulated portion(s) that electrical contact is established between the microelectrode and tissue in which it is embedded.

Microelectrode arrays (polyodes) known in the art most often comprise four microelectrodes attached to a solid support or firmly bundled (tetrode); this combination to constitutes a neural probe. For optimal function the microelectrodes need to be disposed at a particular distance from each other, which is determined by the distance between the electrodes and the neuron in question. A drawback of known microelectrode arrays is their stiffness and size. For this reason they cannot freely move with the tissue into which they are implanted. The shear forces arising between known arrays and surrounding tissue trigger glial responses, eventually causing a glial scar encapsulating them. Such encapsulation is detrimental to their recording capability in view an impaired signal to noise ratio.

There is thus a need in the art for a microelectrode array of improved positional stability once implanted. The improved positional stability should provide improved mechanical adaptation to surrounding tissue and thus a reduced risk of tissue irritation. The need for improved arrays of microelectrodes for positional determination of signals emanating from nerve cells is particularly urgent in regard arrays implanted for long-term use.

OBJECTS OF THE INVENTION

A primary object of the invention is to provide an array of microelectrodes of improved mechanical tissue compatibility.

Another object of the invention is to provide such an array in conveniently implantable form.

A further object of the invention is to provide such an array with improved positional stability in soft tissue.

Still another object of the invention is to provide a combination of arrays of microelectrodes.

Additional objects of the invention will become evident from the following short description of the invention a number of preferred embodiments thereof illustrated in a drawing, and the appended claims.

SUMMARY OF THE INVENTION

According to the present invention is provided a microelectrode array capable of moving with the tissue into which it is implanted, thus being prone to cause less damage to the tissue detrimental to its function. While microelectrode arrays comprising three (triodes) or five (pentodes) or more microelectrodes can be used for the same purpose, the invention is exemplified by an array comprising four microelectrodes. The array of the invention is however not restricted to comprise a few microelectrodes. It can comprise 20 or more, and even 50 or 100 or more microelectrodes. The microelectrode array of the invention has oblong form that is an axial extension which is substantially greater than its radial extension, such as greater by a factor five or ten or more. Consequently, an array comprising a number of oblong microelectrodes also has oblong form since their radial distance is substantially limited. The microelectrode array has a central or gravity axis defined by the microelectrodes in a weighed manner. The distance between any pair of microelectrodes pertaining to an array of the invention is preferably not more than 100 µm, in particular not more than 50 µm or 25 µm; distances exceeding 100 µm can be tolerated at low signal to noise levels. The microelectrodes of an array can have a length exceeding 1000 µm and even 5000 µm. The microelectrodes pertaining to an array of the invention are disposed substantially in parallel, that is, the angular deviation of a microelectrode from the central axis does not exceed 15°, in particular not 10° or 5°.

In particular, according to the present invention is disclosed a microelectrode array of oblong shape having a central array axis, comprising three or more, in particular of from four to seven or more, flexible oblong, electrically co-operating microelectrodes in wire and/or ribbon form of metal and/or electrically conducting carbon and/or electrically conducting polymer disposed substantially in parallel with the array axis, a microelectrode comprising a distal terminal portion, a central portion and a proximal terminal portion, a microelectrode being electrically insulated except for at a section of the distal terminal portion, the section preferably extending from the distal end in a proximal direction; wherein the array further comprises electrically non-conducting microfibres connecting central portions of the microelectrodes in oblique directions in respect of the array axis.

A microelectrode of the array is preferably in wire or ribbon form. However, any other oblong microelectrode can be used in the invention, such as axially extensible microelectrodes of, for instance, meander form, hollow microelectrodes, microelectrodes provided with hooks or other anchoring means at their distal end or at distal portions thereof.

Preferred metals are noble metals such as gold or platinum and their alloys. A preferred electrode insulating material is Parylene. Other preferred electrode body coating materials are polyurethane and silicone but other biocompatible polymer materials may be used as well. Appropriate inorganic materials for electrical insulation such as hafnium oxide can also be used. A preferred method of electrode coating with insulating material is vapour phase deposition.

The distance between two microelectrodes of an array of the invention must not be too great since this would be detrimental to their electrical co-operation. A preferred distance between two co-operating microelectrodes of an array of the invention is from 3 µm to 100 µm, in particular from 5 µm to 20 µm or 50 µm. By co-operating it is understood that the microelectrodes are capable of receiving and transferring signals from a given neuron to a control unit comprising software and data storage means, in which the signals received from neurons are analysed and compared and/or which generates neuron stimulating signals for emission by the microelectrodes. Based on analysis and comparison of the signals the position of single neurons can be determined, as well signals emitted by different neighbouring neurons identified.

A microelectrode of the invention can be essentially straight but may alternatively comprise portions allowing its extension in an axial (proximal-distal) direction. Axially extendable electrodes for use in the invention, such as electrodes comprising meander-formed sections, are disclosed in WO 2009/075625, which is incorporated herein by reference. The microelectrodes of the array of the invention can be of same length or about same length or of different length. Furthermore, a microelectrode array of the invention may also comprise microelectrodes of different design.

It is preferred for at least one microelectrode of an array to be not disposed in a plane defined by two or more other microelectrodes. In an array of four microelectrodes (tetrode) of the invention it is preferred that not more than two microelectrodes are disposed in one and the same plane.

According to a first preferred aspect of the invention an array of the invention comprises an electrode deviation restricting means. The electrode deviation restriction means restricts the radial and axial displacement of the array electrodes in respect of each other while allowing them to move in axial and radial directions within the restriction. A preferred restriction means comprises or consists of electrically non-conducting fibres, which are microfibres in the micrometer or nanometer diameter range, such as having a diameter of from 1 µm to 100 µm or from 2 nm to 200 nm. Particularly preferred are electrospun microfibres.

Preferred fibrous materials include those based on poly (lactide), poly(lactide-co-glycolide), poly(glycolide) and electrospun albumin, ethylene vinyl acetate, polyurethane urea, silk. Other microfibres for use in the invention are natural and synthetic proteinaceous microfibres, such as fibrin microfibres, collagen or collagen based microfibres, laminin microfibres, fibronectin microfibres, cross-linked gelatin microfibres, silk microfibres produced from aqueous protein solutions as disclosed by Viney C and Bell F I (Curr Opin Solid State Mater Sci. (2004) (165-171) but also inorganic microfibres such phosphate glass microfibres, for instance $P_{40}Na_{20}Ca_{16}Mg_{24}$ phosphate glass microfibres disclosed in U.S. Pat. No. 8,182,496 B2. Preferably the microfibres are biodegradable and/or biodissolvable. The microfibres can be of a resilient or non-resilient material.

According to preferred aspect of the invention microfibres comprised by the array form a non-woven structure. It is preferred for fibre to be adhesively attached to two or more microelectrodes and/or to one or more other fibres. Preferably the microfibres are disposed along 50% or more of the axial extension of a microelectrode. It is preferred for a fibre to be biodegradable and/or resilient.

According to another preferred aspect of the invention a preferred kind of microfibres are electro-spun fibres. It is preferred for a microfibre to comprise or consist of a material selected from the group consisting of polyester, in particular polylactide, polyglycolide or mixtures or copolymers thereof, electrospun albumin, electrospun gelatin, electrospun fibrin, electrospun mucus material rich in glycoprotein. It is within the ambit of the invention to provide the device with a net of gelatin and glucose crosslinked using UVB irradiation (Davidenko et al 2016, Masutani et al, 2014). It is also within the ambit of the invention to provide the device with a net of fibrin microfibres by electrospinning fibrinogen, such as by the method of S R Perumcherry et al. disclosed in Tissue Eng Part C Methods 17; (2011) 1121-30 or with a net of poly(lactide-co-glycolide)/fibrin microfibres such as one disclosed by Perumcherry et al. in Tissue Eng Part A 19; 7-8(2012) 849-859. A self-assembling fibrin net can also be produced by applying an aqueous solution of fibrinogen and thrombin rich in calcium directly to a microelectrode array, then cross-linking the microfibres by applying an aqueous solution of plasma transglutaminase and/or factor XIII on the newly formed net for crosslinking. It is preferred for the microfibres connecting microelectrodes or an array or connecting two or more arrays to be arranged sparsely in a manner so as to allow ingrowth of tissue, that is, to form a net-like structure with openings of sufficient size to allow cell ingrowth.

According to a second preferred aspect of the invention two or more microelectrodes or an array are connected by a biocompatible glue that is dissolvable or biodegradable in aqueous body fluid. The fibres comprised by the array can be partially or wholly embedded in the glue.

According to a preferred aspect of the invention the biocompatible glue is one capable of expanding on contact with aqueous body fluid prior to being dissolved or degraded. Upon implantation, aqueous body fluid is taken up by the glue; if expandable the portion of the glue disposed between two or more microelectrodes pushes them apart during the expansion phase, which is followed by a degradation/dissolution phase. An expanding glue displaces the microelectrodes radially outwardly maximally as far as permitted by the microelectrode deviation restricting means. It is preferred for the glue to be selected from the group consisting of gelatin, hyaluronic acid, cellulose derivative such as hydroxypropyl methyl cellulose, and their mixtures or to comprise a member of the group.

According to another preferred aspect of the invention the glue is layered such as to consist of two or more layers of glue, the rate of swelling and/or dissolution and/or degradation in aqueous body fluid of an inner layer preferably being smaller than that of an outer layer. Preferably gelatin in native or crosslinked form is used as a layer material; native gelatin from different sources is known to vary in regard of physical and chemical properties, such as swelling rate and degradation rated in an aqueous environment, Bloom strength, dependence of swelling and dissolution on temperature, etc.; thus gelatin layers of differing in properties can be provided by us of gelatin from different natural sources.

It is preferred for an inner layer to have a higher Bloom strength than an outer layer to ensure that, during their radial displacement against the resistance of the surrounding soft tissue and/or the resistance of the fibres, the microelectrodes are sufficiently supported by the gel so as to not being pressed into it. To provide for radial displacement of microelectrodes by glue swelling the gelatin or other gel forming biocompatible glue should preferably have a Bloom strength of above 100, in particular of above 150. In a combination of outer and inner layers the outer layer comprises or consists, for instance, of native gelatin while the inner layer comprises or consists of cross-linked gelatin. Preferred glues for use in the invention comprise gelatin, hyaluronic acid, cellulose derivative such as hydroxypropyl methyl cellulose and polyethylene glycol.

It is preferred for an inner layer to be crosslinked. The rate of dissolution or degradation of cross-linked gels is slower than that of corresponding non-crosslinked gels. The rate of degradation and/or dissolution is controlled by the degree of cross-linking. Even upon complete degradation or dissolution of outer gel layers cross-linked inner layer(s), for instance gelatin layers crosslinked with glutaraldehyde, are capable of keeping the microelectrodes apart. Outer layers can be built up by treating, such as by dipping, a portion of the microelectrode comprising the dried glue of a higher Bloom strength with an aqueous solution of a glue of a lower Bloom strength, then drying. The application/drying cycle can be repeated as desired. A layered glue of this kind is capable of substantially extending the time from implantation to final anchoring in the tissue of microelectrodes held radially apart by the glue during the time period required for their tissue integration.

It is preferred for the glue to be dissolved and/or degraded within a period of time that is shorter or substantially shorter than the time required for degradation of biodegradable fibres, such as by a factor of 0.5 or 0.2 and even 0.1 or less. It is preferred for the fibres to be biodegradable within a period of up to two or three weeks or one month so as to allow for ingrowth of tissue capable of substituting the positional stabilization of the microelectrodes.

According to a third preferred aspect of the invention a distal and/or central portion of an array microelectrode comprises an eye or a loop. It is preferred for fibres pertaining to an array to be exclusively disposed on microelectrode portions devoid of loops or eyes. The function of the eyes and loops is to allow ingrowth of tissue, thereby further stabilizing the position of the microelectrode in the tissue. The arrangement of loops instead of eyes is advantageous from a standpoint of electrode withdrawal from tissue, which is facilitated in case of a loop by it allowing straightening the electrode on withdrawal, thereby avoiding or at least minimising tissue damage.

According to the present invention is furthermore provided a proto-array designed for implantation into soft tissue by insertion, from which the array of the invention is formed in the tissue upon implantation. The proto array additionally comprises an outer layer of a rigid material, which is biocompatible and dissolves in body fluid upon implantation, in particular dissolves in a short time such as within one or five or ten minutes.

In particular, the rigid material of the outer layer dissolves and/or degrades substantially faster than the glue bonding the microelectrodes, preferably faster than substantial uptake of aqueous body fluid by the glue such as faster than the time required for an uptake of 10% or 20% by weight of aqueous body fluid by the glue. It is preferred for the distance between the axes of two arrays in a combination to be 100 μm or more, in particular 200 μm or more, preferably 500 μm or more.

Electrical co-operation of microelectrodes comprised by an array comprises their control by a control unit. The control unit is equipped with software capable of discerning between electrical signals received the different electrically co-operating microelectrodes. It is preferred for the discernment to be used for determining the position of a signal source, in particular of a neuron.

Direct implantation of an array, a proto array or a combination of two or more arrays can be carried out by disposing the array or the combination of arrays in a surgical incision in soft tissue.

An alternative to direct implantation is indirect implantation by disposing the array or combination of arrays in a cannula, inserting the cannula into soft tissue followed by injecting or inserting it into a channel in tissue filled with aqueous gel, such as disclosed in WO 2016/032384.

Indirect implantation can be also be achieved by inserting a proto-array of the invention into soft tissue where it is transformed into the array of the invention by contact with aqueous body fluid. Implantation of the array other than by means of a cannula can be facilitated by providing an oblong guide attached to the array by gluing or by being incorporated in; the guide is attached in a manner so as to extend substantially in parallel with the array axis and proximally from it. Suitable guide materials comprise rigid polymers such as polystyrene. Metal materials such as stainless steel can also be used. It is preferred to use guides with a polished surface so as to reduce friction against tissue during implantation.

SHORT DESCRIPTION OF THE FIGURES

The figures illustrate preferred embodiments of the electrode array of the invention and stages in their manufacture. For reasons of clarity they are not to scale; the width of single electrodes and electrode arrays is greatly exaggerated.

Figure 1D:
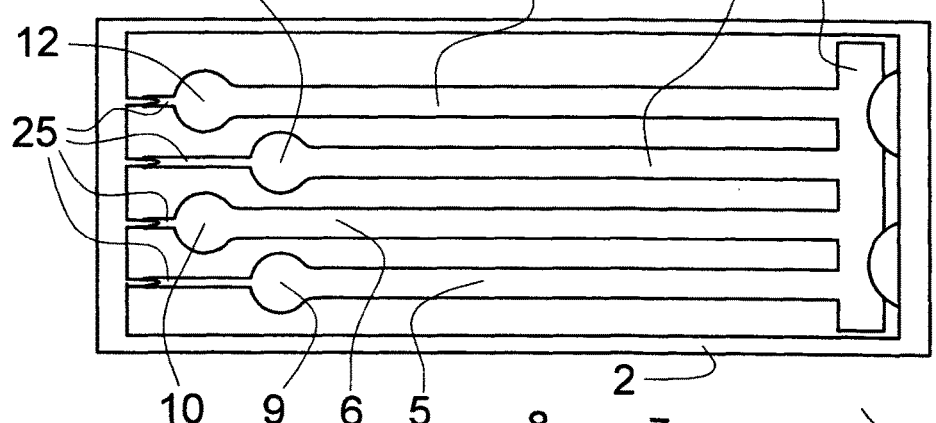
Figure 2A:
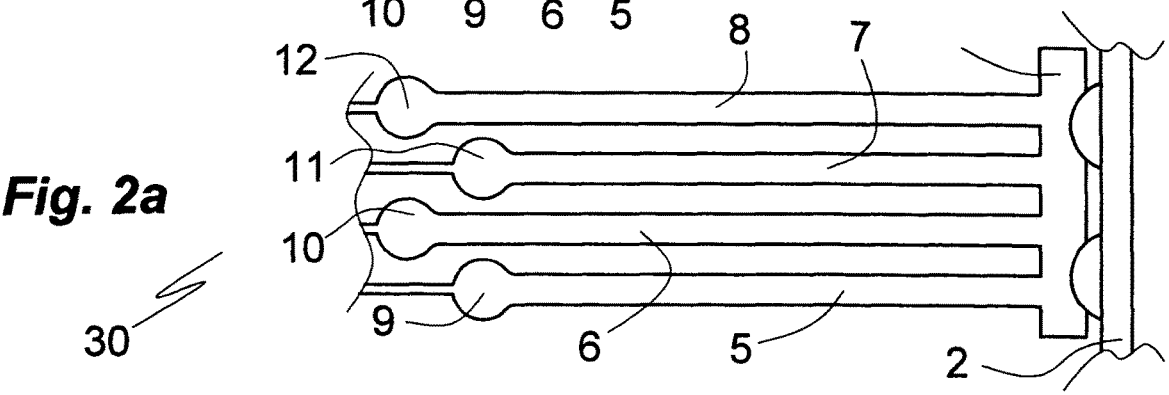
Figure 2B:
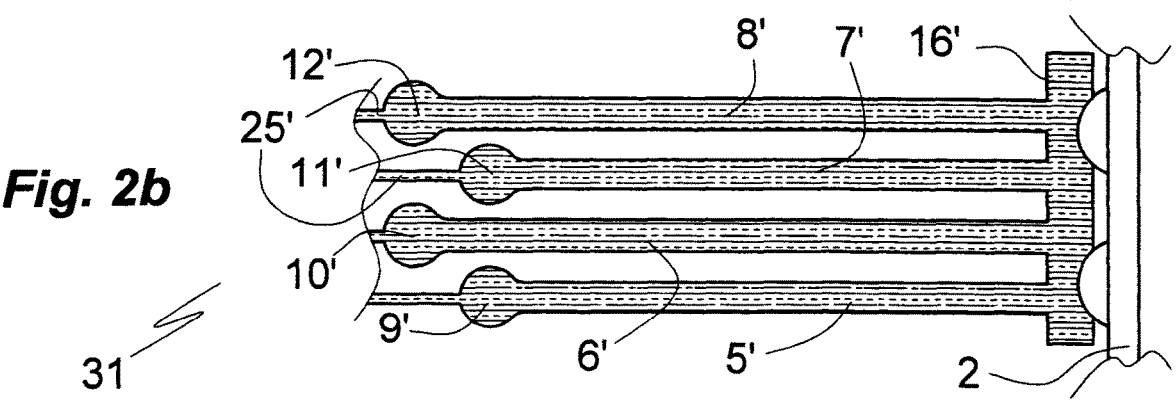
Figure 1B:
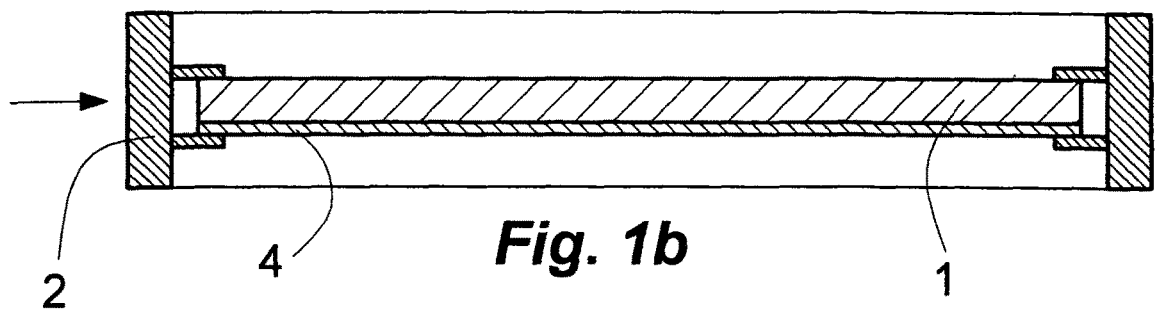
Figure 1C:
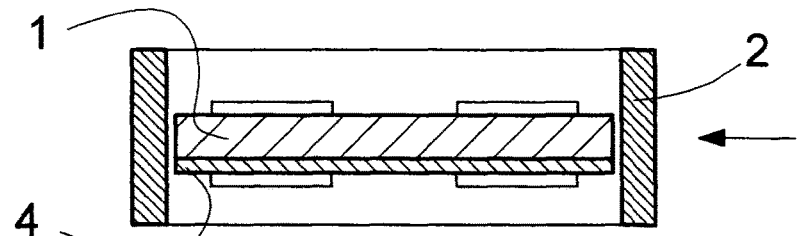
Figure 3A:
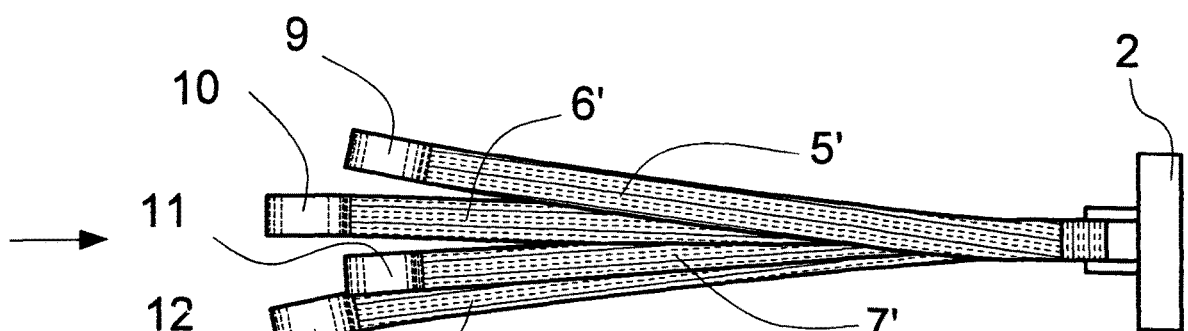
Figure 3B:
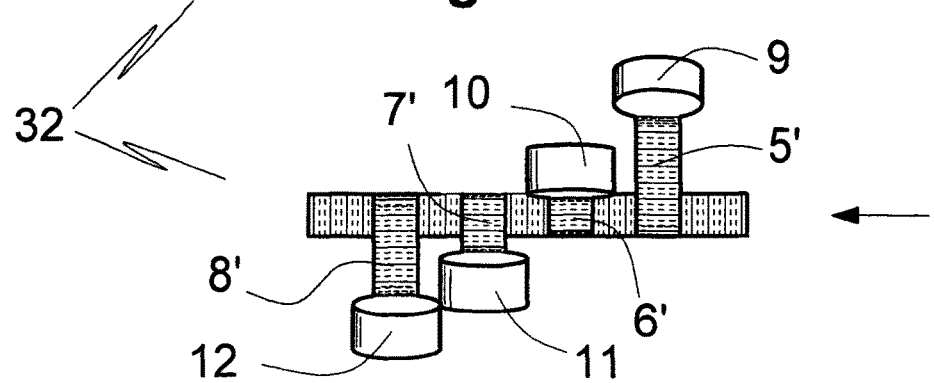
Figure 2C:
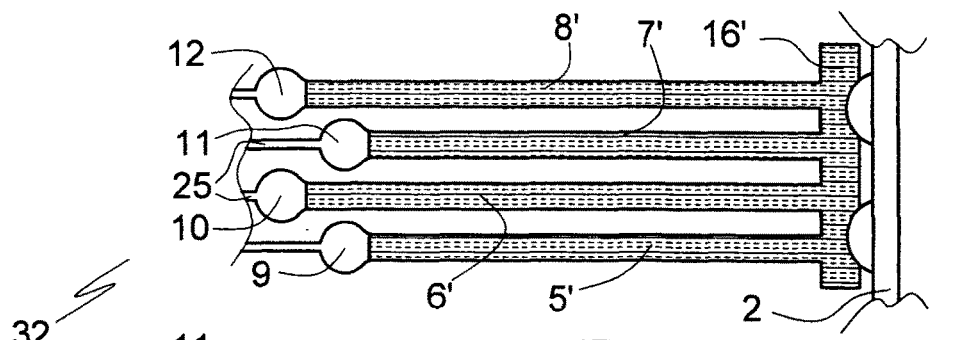
Figure 7A:
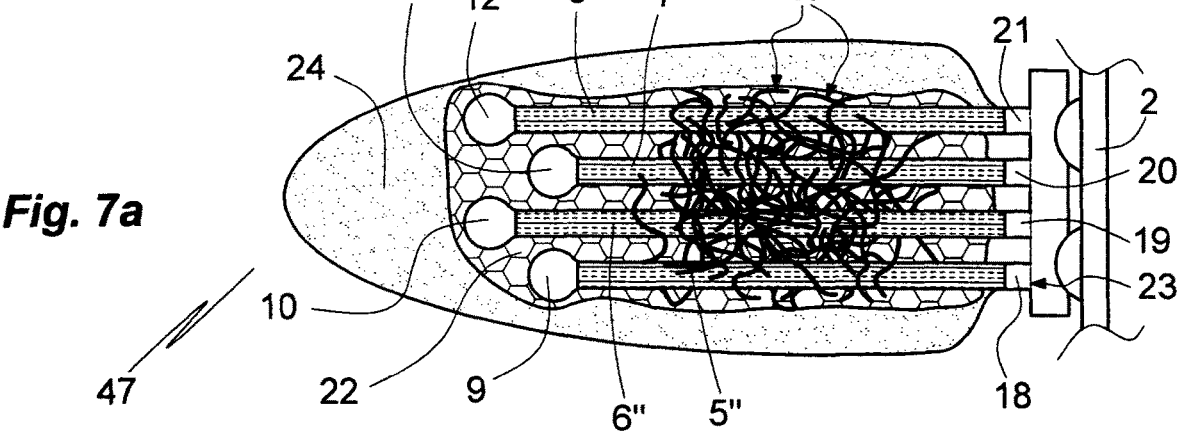
Figure 7B:
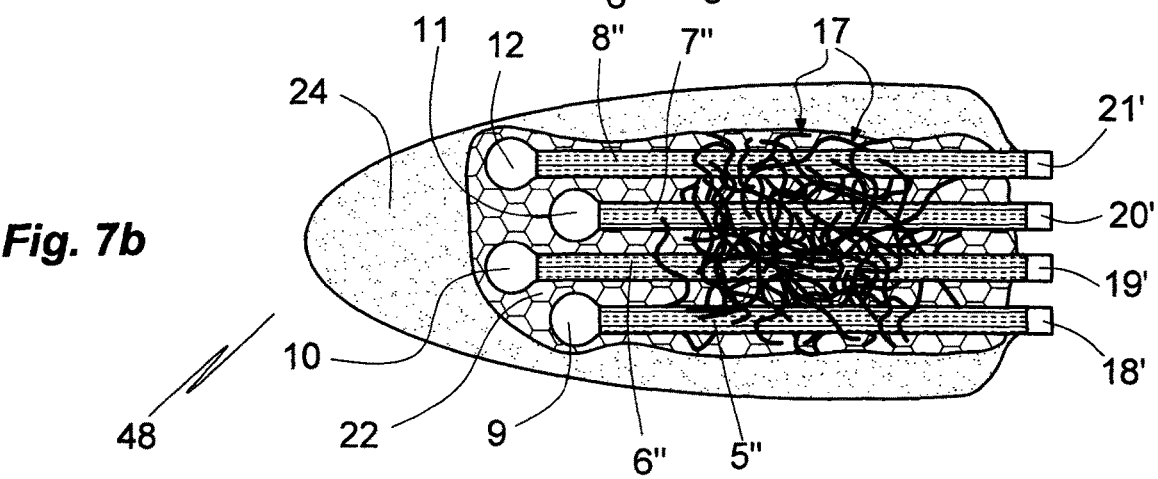
Figure 7C:
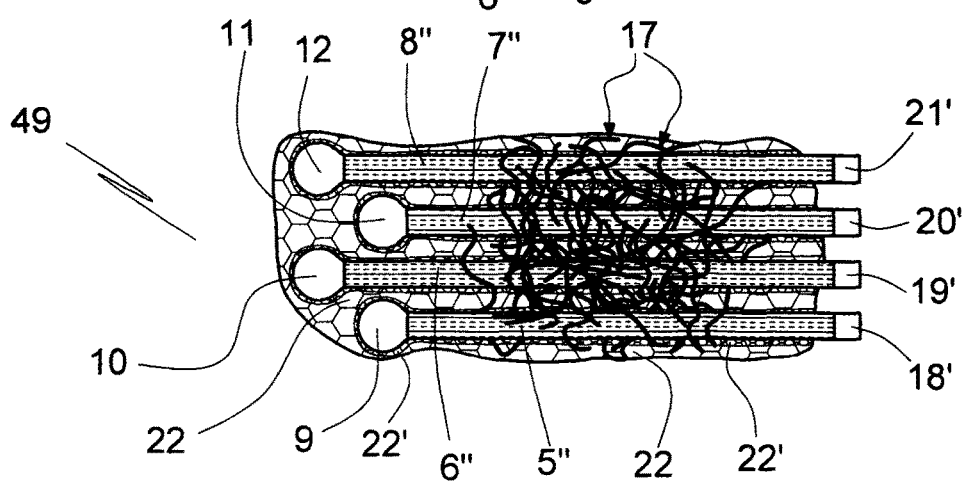
Figure 4A:
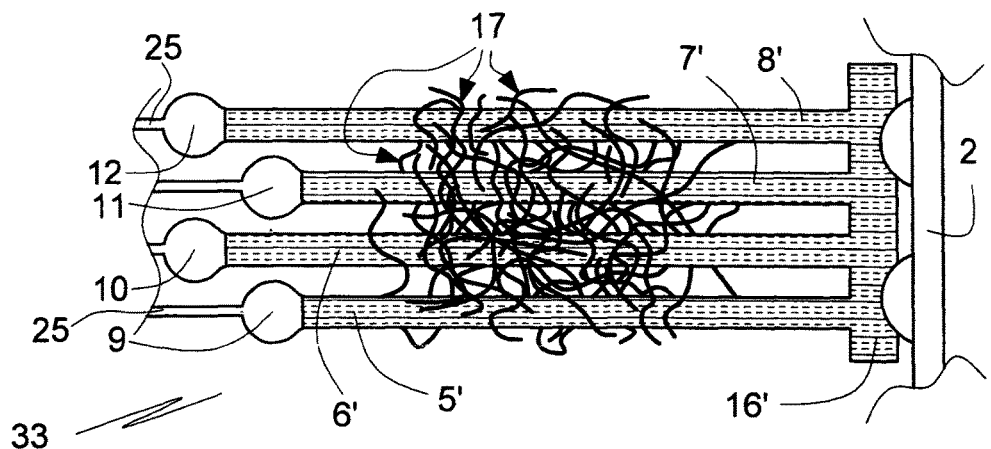
Figure 4B:
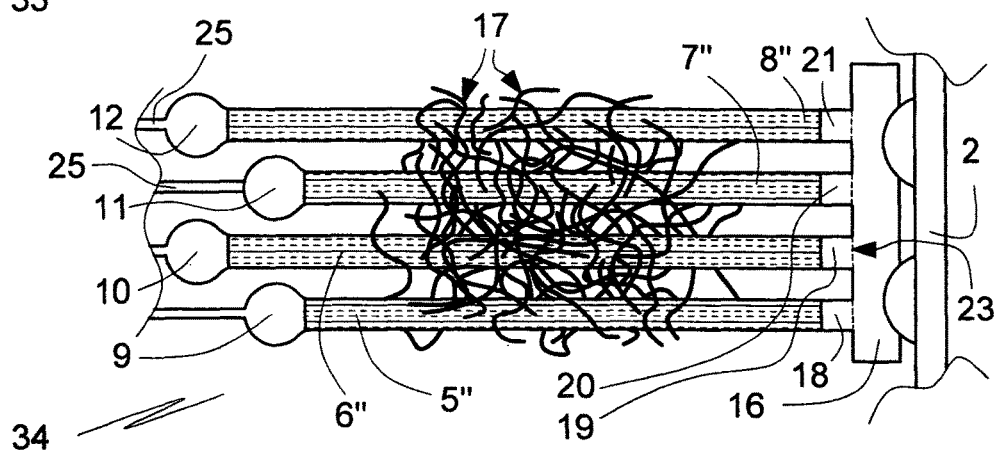
Figure 6A:
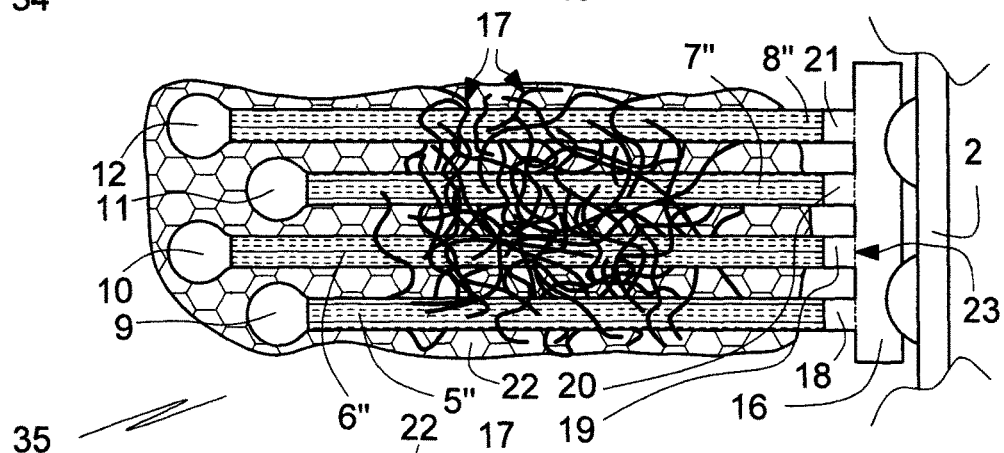
Figure 6B:
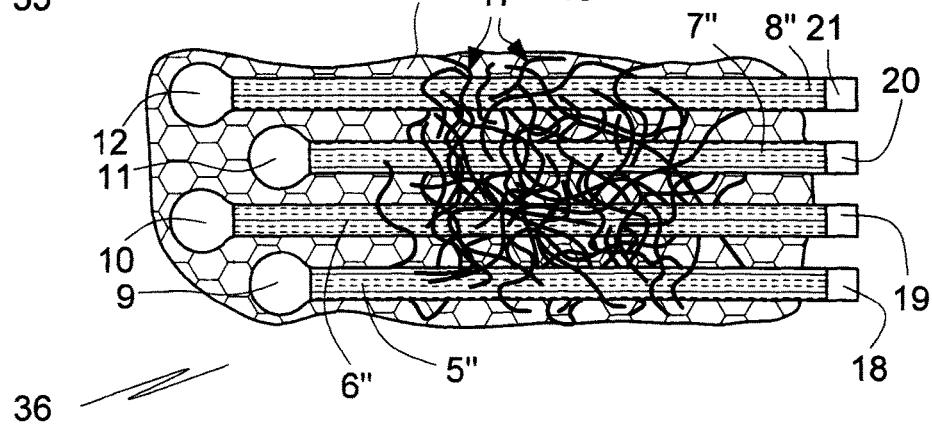
Figure 4C:
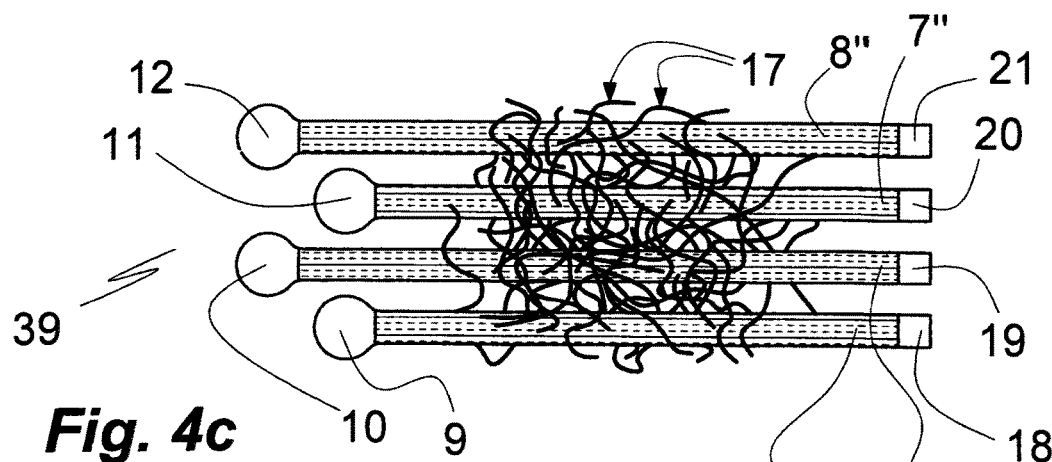
Figure 4D:
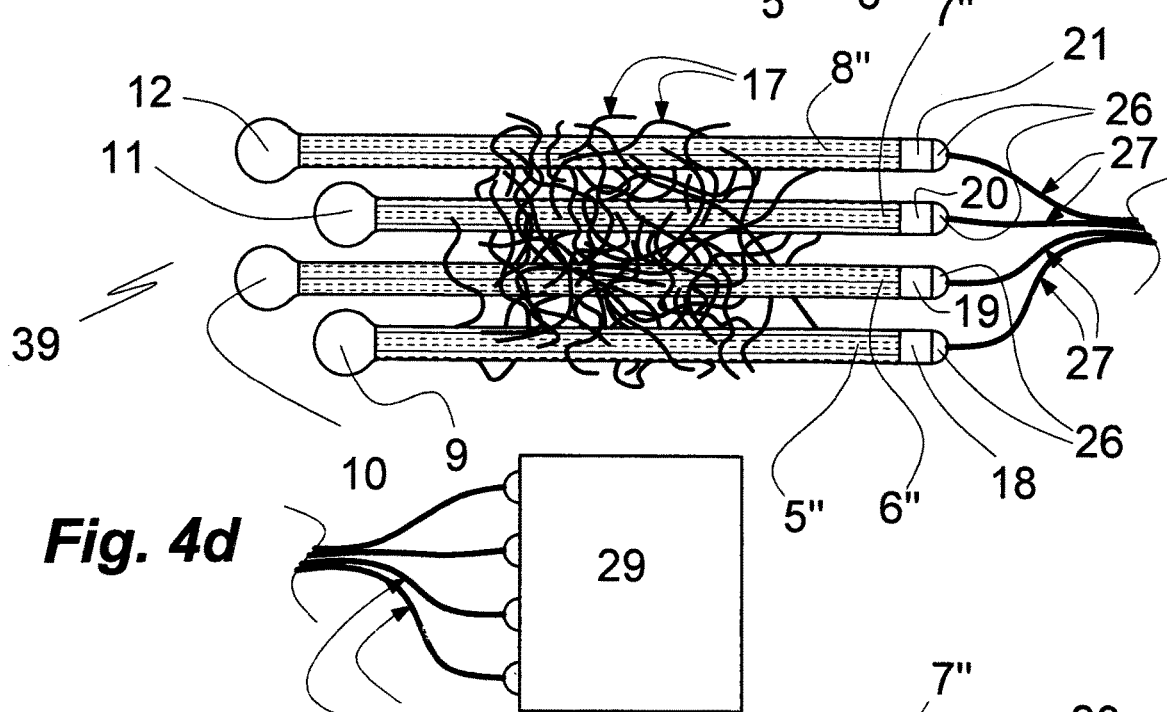
Figure 4E:
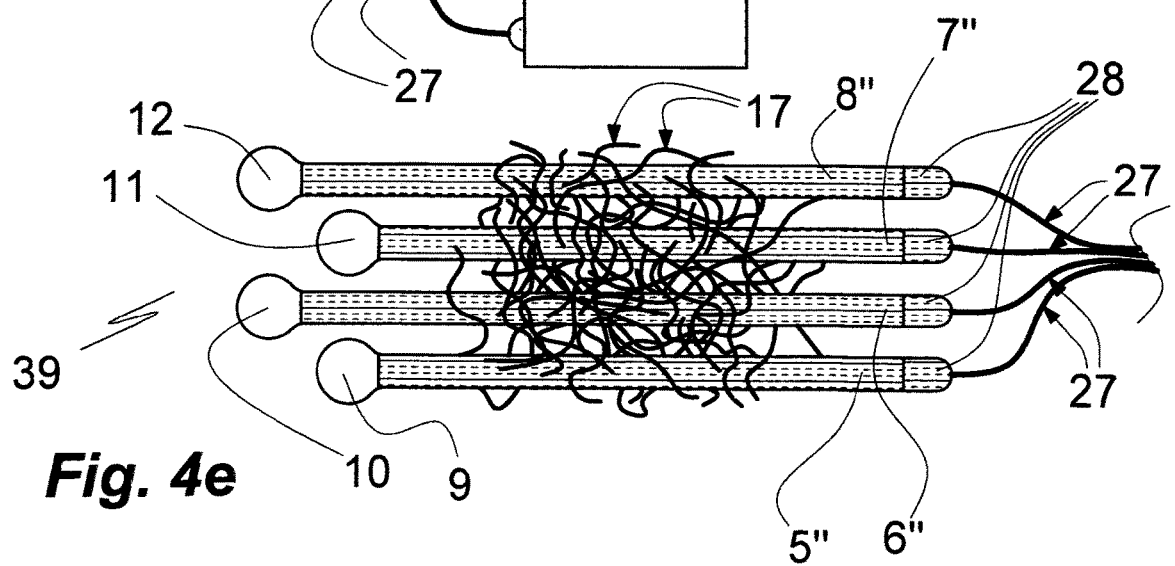
Figure 5A:
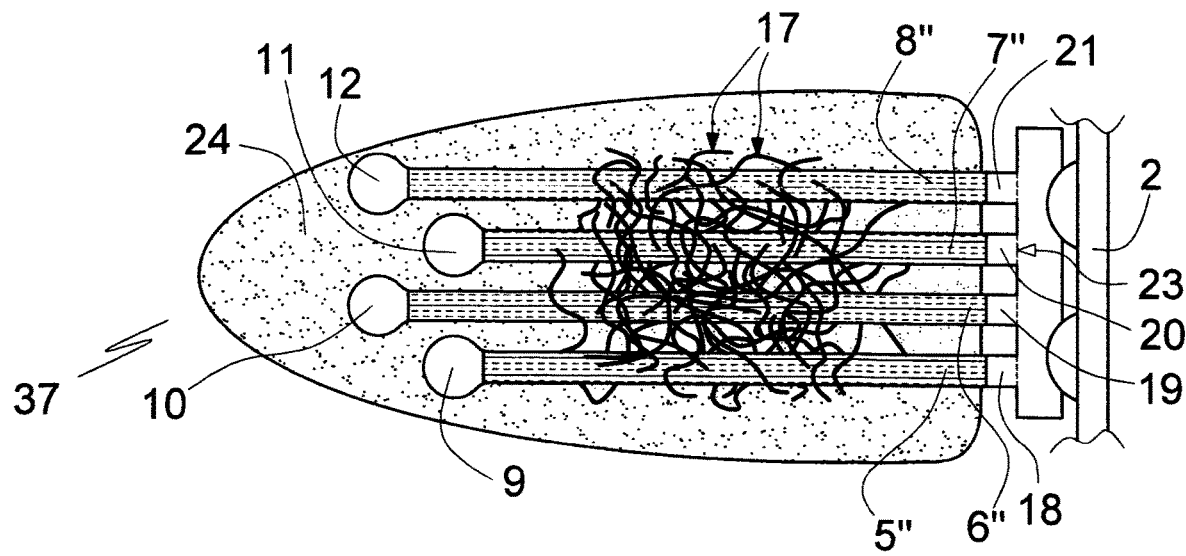
Figure 5B:
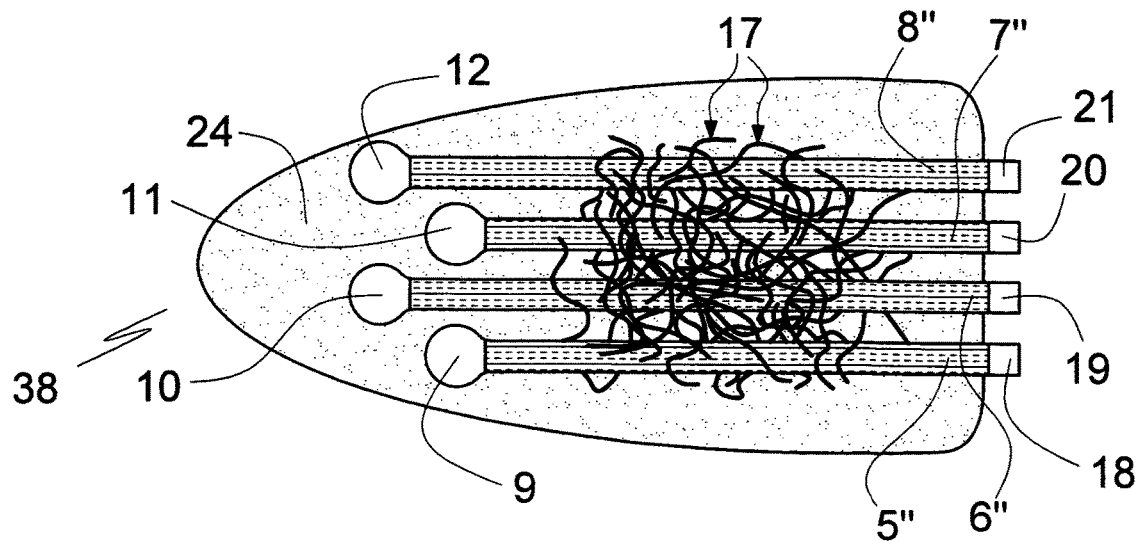

In particular, the figures illustrate:

FIGS. 1a-1c a combination of materials for the manufacture of an array of the invention comprising a sheet of metal on a dissolvable support clamped in a frame, in a top view and in longitudinal A-A and transverse section B-B section;

FIG. 1d an array workpiece cut out from the combination FIGS. 1a-1c, in a top view and clamped in the frame;

FIG. 2a a partial view of FIG. 1d, in the same view;

FIG. 2b the workpiece of FIG. 2a covered, with a layer of insulating material, in the same view as FIG. 2a;

FIG. 2c the workpiece of FIG. 2b with distal terminal electrode portions free of insulating material, in the same view as FIG. 2b;

FIG. 3a the workpiece of FIG. 2c, upon vertical displacement of distal and central portions of its electrodes, in a side view (arrow, FIG. 3b), with distal holding straps not being shown;

FIG. 3b the workpiece of FIG. 3a, in a distal-proximal view (arrow, FIG. 3a), with distal holding straps and the frame not being shown;

FIG. 4a the workpiece of FIG. 2c comprising a network of electrospun fibres, in the same view as in FIG. 2c;

FIG. 4b the workpiece of FIG. 4a with proximal terminal electrode portions lacking insulation, in the same view as FIG. 4a;

FIG. 4c a first embodiment of the array of microelectrodes of the invention made by severing the microelectrode portion of the workpiece and holding straps of Fig. from its base and distal terminal portions, in the same view as FIG. 4b;

FIG. 4d the embodiment of FIG. 4c, upon fastening a flexible insulated lead at the distal end of each of the microelectrodes to provide communication with an array control unit, in the same view;

FIG. 4e the embodiment of FIG. 4c, upon insulation of the distal terminal end, in the same view;

FIG. 5a the workpiece of FIG. 4b with distal and central portions of the array embedded in a matrix of a body fluid dissolvable material, in the same view as FIG. 4b;

FIG. 5b a first embodiment of a proto array of microelectrodes of the invention suitable for implantation by insertion into soft tissue, in the same view as FIG. 5a;

FIG. 6a the workpiece of FIG. 4b physically stabilized by joining electrospun fibres and electrodes with gelatin upon severing holding straps and distal terminal electrode portions from the frame;

FIG. 6b a second embodiment of the array of microelectrodes of the invention made by severing the microelectrode portion of the workpiece of FIG. 6a from its base, in the same view as FIG. 6a;

FIG. 7a the physically stabilized workpiece of FIG. 6a with distal and central portions thereof embedded in body fluid dissolvable material, in the same view as FIG. 6a;

FIG. 7b a second embodiment of the proto array of microelectrodes of the invention suitable for implantation by insertion into soft tissue, in the same view as FIG. 7a;

FIG. 7c a variety of the proto array of FIG. 7b, in the same view;

FIG. 8 a microelectrode of the invention comprising three eyes for tissue integration, in a side view;

FIG. 9 a microelectrode of the invention comprising three loops for tissue integration, in a side view;

FIG. 9a a loop of the microelectrode of FIG. 9, enlarged and in the same view;

FIG. 10 a combination of two microelectrode arrays of FIG. 8 connected by a net-like structure of electrospun microfibres, in a transparent side view;

FIG. 11 the combination of two microelectrode arrays of FIG. 8 embedded in gelatin for direct insertion into soft tissue, in the same view;

FIG. 12 the combination of FIG. 11 embedded in a body fluid dissolvable material, in the same view;

FIG. 13 the combination of FIG. 10 embedded in a body dissolvable material, in the same view.

DESCRIPTION OF PREFERRED EMBODIMENTS

Example 1

The manufacture of a first embodiment of a microelectrode array of the invention is illustrated in FIGS. 1a through 4c. A sheet of thin gold foil 1 attached to the upper face of a sheet of low-molecular polyethylene glycol (PEG) 4 is held by a rectangular frame 2. The electrode array workpiece 30 shown in FIG. 2a in a top view is cut out from the foil 1 along tracing lines 3. For reasons of clarity the thickness of the foil 1 is greatly exaggerated in the figures. The PEG 4 support then is removed by dissolving it in ethanol. The electrode array workpiece 30 (FIGS. 1d, 2a) comprises four electrode bodies 5, 6, 7, 8 with circular distal terminal portions or electrode heads 9, 10, 11, 12, respectively. At their proximal end the electrode bodies 5, 6, 7, 8 are integral with a rectangular base 16 held by the frame 2. At their distal ends the array workpiece 30 the array workpiece 30 is held by narrow holding straps 25 extending from distal portions of the electrode heads 9, 10, 11, 12 fastened, at their other end, in the frame 2.

In the next step the electrode bodies 5, 6, 7, 8 with their heads 9, 10, 11, 12 and the base 16 are covered with an insulating Parylene C layer applied by chemical vapor deposition (CVD) process at low pressure to provide a fully insulated workpiece 31 (FIG. 2b). Other kinds of Parylene, such as Parylene N or D, can also be used. The film thickness can be controlled in the micron range. The work piece 31 illustrated in FIG. 2b comprises four insulated electrode bodies 5', 6', 7', 8', insulted distal heads 9', 10', 11', 12', an insulated base 16', and insulated holding straps 25'. By means of the base 16' and the holding straps 25' the fully insulated workpiece 31 is held by the frame 2.

In the following step the insulation from the heads 9', 10', 11', 12' and the holding straps 25 is removed by laser milling whereby the partly de-insulated workpiece 32 of FIG. 2c is obtained.

The non-insulated heads 9, 10, 11, 12 are then pushed out of their planar disposition so as to make the electrode bodies 5', 6', 7, 8' and the heads assume the disposition illustrated in FIGS. 3a, 3b, in which the holding straps 25 (FIGS. 3a, 3b) and the frame 2 (FIG. 3b) have been omitted.

By electrospinning central sections of the insulated electrode bodies 5', 6', 7', 8 of the partly de-insulated workpiece 32 are provided with a network of polylactide microfibres 17 adhering to the electrode bodies 5', 6', 7', 8' and to each other. The thus obtained partly de-insulated workpiece 32 comprising a non-woven adherent fibrous net-like structure 17 is shown in FIG. 4a.

In a following step illustrated in FIG. 4b the insulation of proximal terminal portions of the electrode bodies 5', 6', 7', 8' of FIG. 4a and of the base 16' is removed by laser milling. The so produced workpiece 34 comprises insulated electrode bodies 5", 6", 7", 8", insulation-free electrode heads 9, 10, 11, 12, and proximal insulation-free terminal portions 18, 19, 20, 21.

In a following step, the workpiece 34 is transformed to a microelectrode array of the invention by attaching flexible insulated leads to the proximal insulation-free terminal portions 18, 19, 20, 21 by soldering or co-melting, then insulating the terminal insulation-free portions by applying a layer of Parylene C; alternatively, a lacquer, silicone or medical-grade epoxy can be applied on desired portions of the lead for insulation. The other ends of the leads are connected to an electronic control unit comprising software for analysis of signals received by each of the electrodes and for emitting neuron stimulating signals from the electrodes. The control unit is programmed for identifying the position of single neurons and discerning between signals emitted by different neurons.

A first microelectrode array 39 of the invention is formed by severing the main portion of the workpiece 34 from the base 16 by laser cutting along tracings 23, and by similarly severing the holding straps 25 from the heads 9, 10, 11, 12. The array 39, FIG. 4c, comprises four electrodes 9, 5", 18; 10, 6", 19; 11, 7", 20; 12, 8", 21 connected by a non-woven net-like structure of adhering fibres.

Each electrode 9, 6"; 10, 7"; 11, 8", 12, 9" of the first microarray 39 of the invention (as well as the electrodes of any other microarray of the invention) can be provided with insulated flexible leads 27 for connecting it to a control unit 29, which may be intra- or extracorporeal. At its distal end, the leads 27 are attached to the insulation free terminal portions 18, 19, 20, 21 of the electrodes 9, 6"; 10, 7"; 11, 8", 12, 9" by soldering, solder points 26 (FIG. 4d).

In a final step the insulation free terminal portions 18, 19, 20, 21 and the solder points 26 are insulated by vacuum phase deposition of Parylene C or by applying a layer of lacquer or silicone or medical grade epoxy to form corresponding insulated proximal terminal portions 28 (FIG. 4e). In the same manner an insulation free terminal portion 18, 19, 20, 21 of any other microelectrode pertaining to an array or a proto array of the invention and its solder point 26 can be insulated.

Example 2

Another embodiment 36 (FIG. 6b) of the microelectrode array of the invention can be produced from the array of FIG. 4c by dipping it with its heads 9, 10, 11, 12 foremost to a depth just short of its terminal portions 18, 19, 20, 21 into an aqueous solution of gelatin, withdrawing it from the solution, and letting it dry, then repeating the procedure until a gelatin body 22 of desired thickness has been formed. Alternatively, spray coating can be used for applying the gelatin layer.

The hard, gelatinous layer 22 thus formed stabilizes the workpiece 36 physically and, when expanding during uptake of aqueous body fluid upon implantation, displaces the microelectrodes of the array in radial directions until an equilibrium is reached between the expanding force of the glue and the counterforce exerted by the tissue and, eventually, by the net-like fibrous structure.

Alternatively, the same embodiment 36 can be produced from the microelectrode array workpiece 34 of FIG. 4b by cutting off the holding straps 25, then performing one or more cycles of gelatin solution dipping, withdrawing, and drying the so obtained workpiece 35 comprising a glue 22 matrix, FIG. 6a. In a final step, the main portion of the workpiece 35 is severed from the base 2 by laser beam cutting along tracings 23 so as to form the second embodiment 36 of the microelectrode array of the invention (FIG. 6b; reference numbers not specifically identified refer to the same elements as in FIG. 6a).

Alternatively, the glue body of array 49 of FIG. 7c comprises two gelatin layers 22, 22' of different composition, the outer layer 22 being of native gelatin whereas the inner layer 22' is of cross-linked gelatin. The can be produced by dipping the array 39 of FIG. 4c first in a solution of native gelatin and drying, then dipping it into a solution of cross-linked gelatin and drying; alternatively by applying a solution of gelatin and glucose, which is then crosslinked by UVB irradiation.

Example 3

Alternatively a microelectrode array of the invention can be manufactured from the workpiece 34 of FIG. 4b by dipping it with electrode heads 9, 10, 11, 12 first to a depth just short of its terminal portions 18, 19, 20, 21 into a concentrated aqueous solution of glucose, withdrawing it from the solution, drying it, and repeating immersion into, withdrawal from the glucose solution and drying until, except for its proximal terminal portions 18, 19, 20, 21 free of insulation, the fully glucose matrix 24 embedded workpiece 37 is obtained (FIG. 5a, reference numbers not specifically identified refer to the same elements as in FIG. 4a).

In a final step the main portion of the workpiece 37 is severed from the base 2 by laser beam cutting along tracings 23 so as to form the second embodiment 36 of the microelectrode array of the invention (FIG. 5b; reference numbers not specifically identified refer to the same elements as in FIGS. 4a, 5a).

Example 4

Still another embodiment of the microelectrode array of the invention can be manufactured from the workpiece 35 (FIG. 6a) by dipping it with electrode heads 9, 10, 11, 12 first to a depth just short of its terminal portions 18, 19, 20, 21 into a concentrated aqueous solution of glucose, withdrawing it from the solution, drying it, and repeating immersion into, withdrawal from the glucose solution and drying until, except for its proximal terminal portions 18, 19, 20, 21 free of insulation, the fully glucose matrix 24 embedded workpiece 47 is obtained (FIG. 7a, reference numbers not specifically identified refer to the same elements as in FIG. 6a). Alternatively, spray coating can be used for providing the glucose embedment.

In a final step the main portion of the workpiece 47 is severed from the base 2 by laser beam cutting along tracings 23 so as to form the fourth embodiment 48 of the microelectrode array of the invention (FIG. 7b; reference numbers not specifically identified refer to the same elements as in FIGS. 6a, 7a).

Example 5

A first embodiment of an electrode 40 for use in the microelectrode array of the invention illustrated in FIG. 8 comprises an insulated elongate electrode body 41 of which the proximal end comprising means for electrically connecting it to control unit is not shown. The electrode body 14 comprises three eyes 43, 44, 45, which allow tissue to grow into it, thus positionally stabilizing the electrode 40 in the tissue. At is distal end the electrode body 41 ends in an elliptic head 42' which is not insulated.

Example 6

A second embodiment of an electrode 40' for use in the microelectrode array of the invention illustrated in FIG. 9 comprises an insulated elongate electrode body 41' of which the proximal end comprising means for electrically connecting it to control unit is not shown. The electrode body 41' comprises three loops 43', 44', 45', which allow tissue to grow into it, thus positionally stabilizing the electrode 40' in the tissue. The loops 43', 44', 45' formed by bending the electrode body 41' allow the electrode 40' to be withdrawn from the tissue while not damaging it. At is distal end the insulated electrode body 40' ends in an elliptic head 42', which is not insulated.

Example 7

A combination 50 of two microelectrode arrays 51, 56 of the invention is shown in FIG. 10. Each of the arrays 51, 56 comprises four electrodes of the kind illustrated in FIGS. 8 and/or 9 identified by their non-insulated electrode heads 52, 53, 54, 55, array 51, and 57, 58, 59, 60, array 56. The electrodes comprise either three eyes 61, 62, 63 or two eyes 64, 65. Instead of eyes 61, 62, 63, 64, 65 one or several loops 44' of FIGS. 9, 9a can be arranged on the electrodes. While the proximal ends of the combination are not shown, it should be understood that each electrode is electrically connected to a control unit (not shown), which comprises software capable of analysing the signals of the electrodes pertaining to one array independent of the analysis of signals of the other array, and presenting the result of the analysis visually and/or graphically. The electrodes of the arrays 51, 56 are connected by a non-woven structure of microfibres 66 deposed on the electrodes by electrospinning.

Example 8

For improved tissue insertion stability, a central portion of the combination 50 of microelectrode arrays 51, 56 of Example 7 is soaked with aqueous aqueous gelatin and dried to provide the modified combination 70 fully or partially embedded in gelatin 71. All other reference numbers of FIG. 11 refer to elements corresponding to those identified in FIG. 10. In addition to conferring physical stability the gelatin 71 glue provides a means for radially displacing the electrodes of the arrays 51, 56 upon contact with aqueous body fluid which, prior to dissolving the gelatin 71 makes it expand. By the expansion the electrodes of the arrays 51, 56 are displaced in radial directions so as to increase their distance from each other.

Example 9

The modified combination 70 of microelectrode arrays 51, 56 of Example 8 can be further modified by embedding it, except for a proximal terminal portion (not shown), in a carbohydrate and/or proteinaceous matrix 81 to form the combination of 80 of microelectrodes of FIG. 12. The matrix layer 81 is adding further insertion stability to the combination of microelectrode arrays 80 thus obtained. It is dissolved within a short time upon insertion into the tissue.

Example 10

The combination 50 of the microelectrode arrays 51, 56 of Example 7 can be alternatively modified by substituting the gelatin glue binding the electrodes and non-woven fibres by the carbohydrate/matrix 60 of EXAMPLE 9 so as to obtain the carbohydrate and/or proteinaceous matrix 81 embedded combination 90 of electrode arrays 51, 56 of FIG. 13.
Materials and Methods
Metal Foil.

Electrode strips were cut out from a gold foil of about 2 μm thickness held in a frame. The strips were provided with Parylene C insulation by vapour phase deposition. The insulation was then removed by heating with a laser beam from desired zones. The non-insulated distal zone had a length of from about 10 μm to about 30 μm. To improve its support one face of the foil can be provided with a layer of a material dissolvable in water or an organic solvent such as ethanol. A preferred support material is low molecular weight polyglycol, which is soluble in ethanol.
Biocompatible Glue.

Gelatin in native or crosslinked form can be used. To provide for radial displacement of microelectrodes by glue swelling the gelatin or other gel forming biocompatible glue should have a Bloom strength of above 100, in particular of above 150. The biocompatible glue can be applied in layers. Inner layer(s) should have a higher Bloom strength than outer layer(s) to ensure that, during their radial displacement against the resistance of the surrounding soft tissue and/or the resistance of the fibres, the microelectrodes are sufficiently supported by the gel so as to not being pressed into it. Alternatively, the inner layer is crosslinked. The rate of dissolution or degradation of cross-linked gels is slower than that of corresponding non-crosslinked gels. Their rate of degradation and/or dissolution is controlled by their cross-linking degree. Even upon complete degradation or dissolution of outer gel layers cross-linked inner layer(s), for instance gelatin layers crosslinked with glutaraldehyde, are capable of keeping the microelectrodes apart. Outer layers can be built up by treating, such as by dipping, a portion of the microelectrode comprising the dried glue of a higher Bloom strength with an aqueous solution of a glue of a lower Bloom strength, then drying. The application/drying cycle can be repeated as desired. A layered glue of this kind is capable of substantially extending the time from implantation to final anchoring in the tissue of microelectrodes held radially apart by the glue during the time period required for their tissue integration.
Electrospinning.

Preferred solution electrospinning materials for use in the invention are cross-linked gelatin, polyglycolide, polylactide, and polylactide-co-glycolide, ethylene vinyl acetate.

REFERENCES

D H Reneker and I C Chun, *Nanometre diameter fibres of polymer, produced by electrospinning.* Nanotechnology 7 (1996) 216-223;

Nayak R et al., *Recent advances in nanofiber fabrication techniques.* Textile Research Journal 82; 2 (2012) 129-147;

Matthews J A et al., *Electrospinning of Collagen Nanofibers* Biomacromolecules 3; 2 (2002) 232-238;

Leach M K et al., *Electrospinning Fundamentals: Optimizing Solution and Apparatus Parameters.* J Vis Exp 47 (2011) e2494, doi:10.3791/2494 (2011);

Davidenko N et al., R. E, *Optimization of UV irradiation as a binding site conserving method for crosslinking collagen based scaffolds.* J Mat Sci. Materials in Science 27 (2016)14;

Masutani E M et al., *Increasing thermal stability of gelatin by UV induced cross-linking with glucose.* Int J Biomater 2014:979636.

The invention claimed is:

1. A microelectrode array of oblong shape having a central array axis, comprising three or more flexible oblong, electrically co-operating microelectrodes of metal and/or electrically conducting carbon and/or electrically conducting polymer disposed substantially in parallel with the array axis such that the angular deviation of a microelectrode does not exceed 15° with respect to the array axis, the microelecrodes comprising a distal terminal portion, a central portion, and a proximal terminal portion, the microelectrodes being electrically insulated except for at a section of the distal terminal portion, the distance between any pair of microelectrodes being no more than 100 µm;

the array further comprising electrically non-conducting microfibres connecting central portions of the microelectrodes in oblique directions in respect of the array axis; wherein at least one microelectrode of the array is not disposed in a plane defined by two or more other microelectrodes.

2. The array of claim 1, wherein the microfibres are non-woven.

3. The array of claim 1, wherein the microfibres are adhesively attached to two or more microelectrodes and/or to one or more fibres.

4. The array of claim 1, wherein the microfibres are disposed along 50% or more of the axial extension of a microelectrode.

5. The array of claim 1, wherein the microfibres are biodegradable.

6. The array of claim 1, wherein the microfibres are resilient.

7. The array of claim 1, wherein the microfibers are electro-spun fibre.

8. The array of claim 1, wherein the microfibers comprise or consist of a material selected from the group consisting of polyester, electrospun albumin, mucus material rich in glycoprotein.

9. The array of claim 1, wherein two or more microelectrodes are connected by a biocompatible glue that is dissolvable and/or biodegradable in aqueous body fluid.

10. The array of claim 9, wherein the biocompatible glue is one capable of expanding on contact with aqueous body fluid prior to being dissolved or degraded.

11. The array of claim 9, wherein the glue is selected from the group consisting of gelatin, hyaluronic acid, cellulose derivative, and mixtures thereof or comprises a member of the group.

12. The array of claim 9, wherein the glue is layered.

13. The array of claim 12, wherein the rate of swelling and/or dissolution and/or degradation in aqueous body fluid of an inner layer of the glue is slower than that of an outer layer of the glue.

14. The array of claim 12, wherein an outer layer of the glue comprises or consists of native gelatin and an inner layer of the glue comprises or consists of cross-linked gelatin.

15. The array of claim 12, wherein an inner layer of the glue has a Bloom strength of above 100.

16. The array of claim 9, wherein the microfibres are partially or fully embedded in the glue.

17. The array of claim 1, wherein a distal and/or a central portion of a microelectrode comprises an eye or a loop.

18. The array of claim 17, wherein the microfibres are exclusively disposed on microelectrode portions devoid of loops or eyes.

19. The array of claim 1, wherein the angular deviation of a microelectrode with respect to the array axis does not exceed 10°.

20. The array of claim 1, wherein electrical co-operation comprises control by a control unit.

21. The array of claim 20, wherein the control unit comprises software capable of discerning between electrical signals received different electrically co-operating microelectrodes.

22. The array of claim 21, wherein determining the position of a signal source is based on such discernment.

23. A system comprising two or more microelectrode arrays of claim 1.

24. The system of claim 23, wherein the two or more arrays are connected by electrically non-conducting microfibers in oblique directions relative to axes of the arrays.

25. The system of claim 23, wherein the arrays are fully or partially embedded in a material soluble in aqueous body fluid.

26. The system of claim 25, wherein the material consists of or comprises carbohydrate.

27. The system of claim 23, wherein the distance between the axes of the arrays is 100 µm or more.

28. The system of claim 23, further comprising a control unit.

29. The system of claim 28, wherein the control unit is configured to discern between electrical signals received from different electrically co-operating microelectrodes.

30. The system of claim 29, wherein the position of a neuron is determined based on discerning between electrical signals received from different electrically co-operating microelectrodes.

31. The array of claim 1, wherein the microfibre comprises or consists of polylactide, polyglycolide or mixtures or copolymers thereof.

32. The array of claim 9, wherein the glue comprises a hydroxypropyl methyl cellulose.

* * * * *